United States Patent [19]

Kosti

[11] 4,229,410

[45] Oct. 21, 1980

[54] BACTERIOSTATIC DEODORANT WATER COLORING TOILET ELEMENT

[76] Inventor: Carl M. Kosti, P.O. Box 1777, Troy, Mich. 48084

[21] Appl. No.: 877,373

[22] Filed: Feb. 13, 1978

[51] Int. Cl.² .................. A61L 9/00; A61L 13/00; E03D 9/02

[52] U.S. Cl. .................. 422/28; 4/224; 4/225; 422/36; 422/37; 424/76

[58] Field of Search .................. 424/76; 422/28, 36, 422/37; 4/224

[56] References Cited

U.S. PATENT DOCUMENTS

| | | | |
|---|---|---|---|
| 2,464,043 | 3/1949 | Kamlet | 424/76 |
| 2,993,214 | 7/1961 | Franco | 4/228 |
| 3,290,698 | 12/1966 | Joyner et al. | 4/228 |
| 3,597,772 | 8/1971 | Leavitt et al. | 4/222 |
| 3,655,129 | 4/1972 | Selner | 424/76 |
| 4,107,312 | 8/1978 | Wegner et al. | 424/76 |
| 4,117,110 | 9/1978 | Hautmann | 424/76 |

FOREIGN PATENT DOCUMENTS

| | | | |
|---|---|---|---|
| 2400273 | 7/1975 | Fed. Rep. of Germany | 424/76 |
| 2506861 | 8/1975 | Fed. Rep. of Germany | 424/76 |
| 412196 | 5/1963 | Japan | 424/76 |
| 40-28118 | 12/1965 | Japan | 424/76 |
| 47-13640 | 4/1972 | Japan | 424/76 |
| 49-20337 | 2/1974 | Japan | 424/76 |
| 6812254 | 3/1970 | Netherlands | 424/76 |
| 7309629 | 1/1974 | Netherlands | 424/76 |
| 1502852 | 3/1978 | United Kingdom | 424/76 |

*Primary Examiner*—Allen J. Robinson
*Attorney, Agent, or Firm*—Gifford, VanOphem, Sheridan & Sprinkle

[57] ABSTRACT

A toilet element having bacteriostatic and/or deodorizing and/or coloring components contained within a water soluble, water sensitive or water swellable resinous article. The element is made functional by merely contacting it with water to thereby release a determined amount of the active agents in the environment until all or part of the element is dissolved in the water.

4 Claims, 1 Drawing Figure

BACTERIOSTATIC DEODORANT WATER COLORING TOILET ELEMENT

BACKGROUND OF THE INVENTION

A bacteriostatic agent is a substance that retards the life processes of the bacteria and although it does not kill them instantly through continuous inhibition it will eventually result in death for the bacteria. Heretofore, cosmetic toiletries have been made with water insoluble plastic or plastic derivative containers which when placed in the water tank of the toilet release a liquid or water soluble substance containing one or more of the aforementioned agents. The substance is generally colored employing one of the many commercially available dyes and upon exhaustion of the agents in the container, indicated by absence of color in the fluid, the water insoluble plastic or plastic derivative container is removed from the toilet tank and discarded. All of the presently available toilet elements are unequivocally activated by the water pressure in the tank or the amount of water in the tank and in the absence of either factor the element is nonoperable and useless. These items are expensive to manufacture; some parts are disposable; they discolor the inner surfaces of the water tank; they are difficult to use; they have a structural part to maintain them in position in the tank; and they are costly to the consumer.

This invention has for an object the production of a toilet element which does not contain any water insoluble part or component thereof, is not suspended in the water tank by any hanging part and usually is not visible.

A related object is to provide a completely water soluble entity containing the active ingredients dispersed, embedded, suspended or emulsed in the water sensitive, water soluble or water swellable binding agent. A further object of the invention is to provide an inexpensive and long lasting toilet article for the consumer.

The novel object of the invention is that it is totally independent of water pressure in the tank or the water level (the amount of the water) in the tank.

The central object of the invention is to provide a water soluble toilet element containing therein bacteriostatic and/or deodorizing and/or coloring agents and is active only when contacted with water and is adapted to be placed in such a position in the toilet that such contact occurs only during the flushing of water whereby the normal mechanical and structural components of the toilet open to allow such contact with water and at the completion of the flushing cycle the mechanical and structural components mechanically close to disallow further contact of the element with water.

Still other objects will become apparent from the following description.

SUMMARY OF THE INVENTION

The above objects are accomplished by the following invention which in its broader aspect involves the preparation and use of a toilet element or article containing (1) a water sensitive, water soluble or water swellable binding agent, (2) a bacteriostatic and/or deodorizing and/or coloring ingredients dispersed, embedded, suspended, or emulsed within the water sensitive, water soluble or water swellable binding agent and (3) dispersants, antioxidants, plasticizers, stabilizers, hardeners, soaps and/or detergents, fillers, water and/or organic solvents and other processing and supportive agents; which toilet element when placed in such a location in the toilet unit is exposed to water only when the toilet is flushed and is automatically isolated or partially isolated from the water when the unit is not operational. Further the unit is not dependent on water pressure or amount of water in the tank.

In the process, composition, and usage of the invention the toilet element is placed in the upper portion of the drain aperture in the tank which receives the inflow of water from the float valve through a rubber or plastic tube and drains directly into the main drain below the tank proper, circumventing the water in the tank when the toilet is flushed and is isolated or semi-isolated from the water when the float valve is closed at the end of the flushing cycle. This process allows enough of the element to be dissolved and carried directly into the toilet bowl (as opposed to being dissolved in the tank) where the action of the active ingredients are mostly needed. The element of this invention is effective until completely dissolved as indicated by the absence of color in the toilet bowl water and a fresh element inserted in the aforesaid location to repeat the process.

DESCRIPTION OF THE PREFERRED EMBODIMENT

Figure 1:
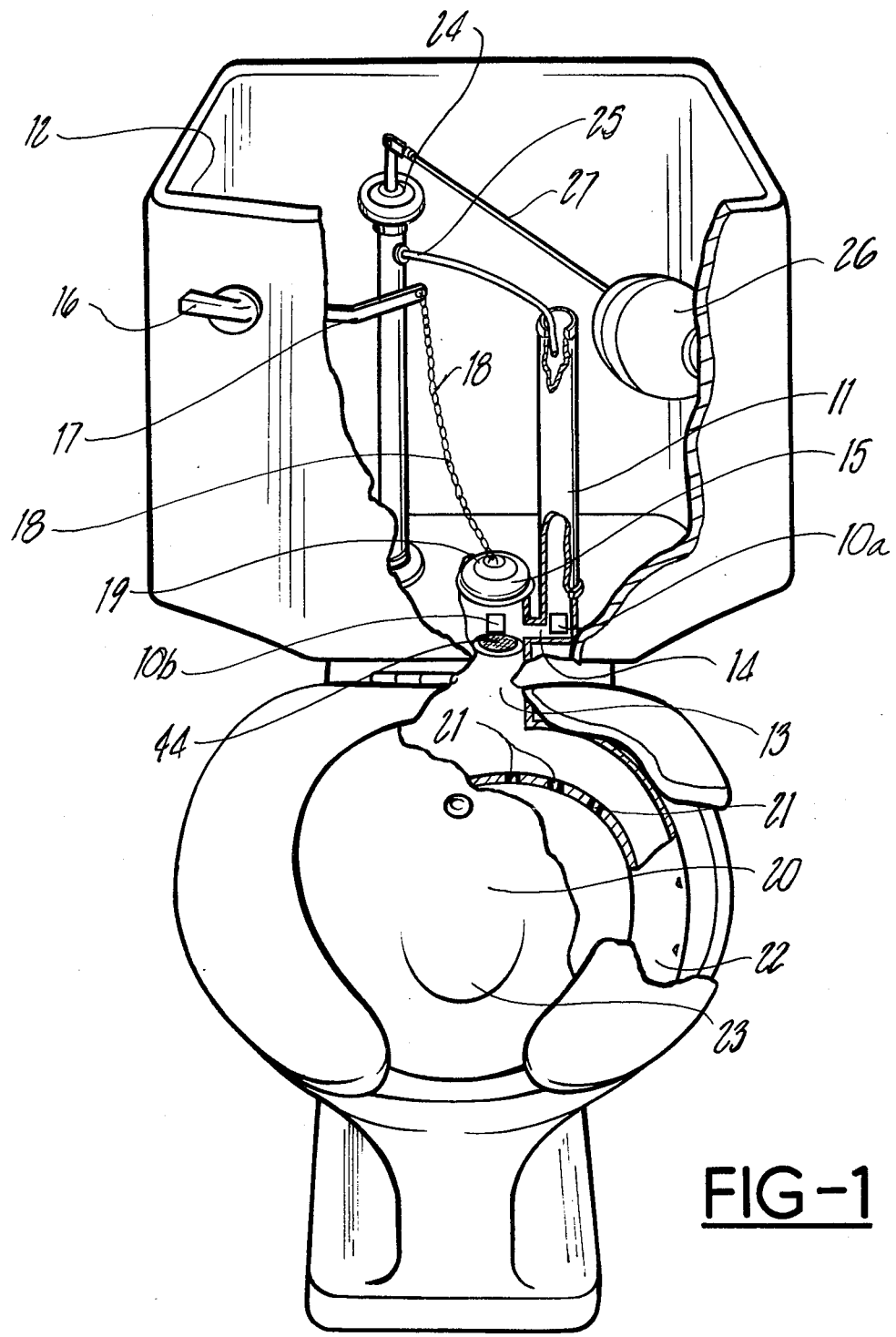
FIG. 1 is an elevational view with portions in section of a toilet employing the device of the present invention.

Other features and advantages of the present invention will be made more apparent as this description proceeds. In utilizing the process and composition of the element of this invention, and in reference to FIG. 1, the element indicated generally by reference numeral 10(a) and 10(b) is preferably placed in the aperture of the upright portion of the drain tube 11 located near the center of the bottom of the toilet tank 12 and connected to the main drain tube 13 via a small opening 14 below the plastic or rubber closure cup 15. The element is activated by a series of related actions initiated by depressing the handle 16, lifting horizontal bar 17 which is connected by vertical chain 18 to the partially rotating unit 19 attached to rubber or plastic cup 15, elevating the cup 15 from its sealant position over an aperture of main drain tube 13 allowing water from tank 12 to flow into the bowl 20 through small openings 21 located around the circumference of the bowl rim 22 and to thereby remove the contents of the bowl through the sewage drain 23. At the start of the flushing cycle, float valve 24 opens to allow a flow of water through the small rubber or plastic tube 25 into the upright drain tube 11 and into the main drain 13. This action of the float valve is initiated by lowering the water level in the tank which in turn lowers the floating ball 26 connected to the floating valve 24 via the float rod 27 until the process is reversed when the cycle is completed and the float ball 26 is raised by the increase of volume of water in the tank until the water level reaches a desired measure in the tank, shutting off the inflow of water through the float valve 24 into the upright drain tube 11 wherein the toilet element 10a is positioned. The element 10 of this invention may be positioned in the upright tube 11 as shown at 10a, preferably, or it may be located in the main drain 13 as shown at 10b which in either case is not directly connected to the water in the tank proper. It functions completely apart from the water in the tank.

To prolong the activity of the toilet element a small plastic or wire mesh filtering basket 44 of proper diameter may be placed either in the upright tube 11 or in the main drain tube 13 and left in position after the initial placement. The basket 44 may have small apertures in its entire circumference, or part of, to facilitate the escape of water into the toilet bowl.

The rate of dissolution of the toilet element 10 in the water is dependent on certain factors of which some are:

1. The chemical and physical characteristics of the binding agent.
2. The duration of exposure to the running water.
3. The amount of water acting on the element.
4. The duration and temperature of the cure of the binding agent during manufacture.
5. The presence of chemical inhibitors i.e. reacting the binding agent with with another compound or salt to alter the solubilitiy constant of the element.
6. The concentration of the binding agent.
7. The temperature of the water.

Using the above factors as guides the toilet element 10 may be made to last from about 10 flushing cycles and up to, but not limited to, about 1,000 cycles by simply altering one or more of the above factors.

The preferred materials for use as the hydrophilic binding agent which contains the active elements of the invention are water soluble polymerizing acrylonitrile; butadiene and styrene monomers; acetal copolymers; acetal homopolymers; acrylics; alkyds; allyls; aminos; cellulosics; epoxies; fluoroplastics; furans; ionomers; nitrile barrier resins; nylons; phenolics; phenylene-oxide based resins; poly(amide-imide); polyaryl ethers; polyaryl sulfones; polybutadienes; polybutylenes; polycarbonates; polyesters; polyethersulfones; polyethylenes; polyimides; polyphenylene sulfides; polypropylenes; polystyrenes; polysulfones; polyurethanes; polyvinyls; silicones; salts of heavy metals cellulose sulfates; other water soluble materials such as gelatin and gelatin derivatives of which gelatin is the main radical; colloidal albumen; hydrolysed polyvinyl acetate; hydrolysed cellulose acetate hydrolysed to an acetyl content of 19–26%; polyacrylamide or an imidized polyacrylamide; zein; polyvinyl alcohol; a vinyl alcohol polymer containing urethane carboxylic acid groups; or containing cyanoacetyl groups such as the vinyl alcohol-cyanoacetate vinyl copolymer; or a polymer material which results from polymerizing protein with a monomer having a vinyl group. Other naturally occurring colloids such as agar-agar, Irish moss, pectin, starch, shellac, rosin, xanthene gums, gum arabic, guar gum; naturally occurring or synthetic alginates such as salts of water soluble heavy metals of sodium, potassium and magnesium; and any combination of mixtures thereof.

The most suitable members of these classes comprise those colloids which are water soluble, water sensitive or water swellable such as gelatin, zein, xanthene gums, guar gum, gum arabic, alginates, cellulose acetate, metal salts of cellulose sulfate, cellulose ether phthalate, copolymer of 80% acrylic acid and 20% ethyl acrylate, polytriglycol adipamide, polyvinyl alcohol, poly(ethylene)oxide, polyacrylic acid, styrene-maleic anhydrite copolymer, polyurethanes, polyacrylamides, poly(vinyl pyrrolidone) and mixtures thereof.

If desired compatible mixtures of two or more of these compounds may be employed for dispersing the active agents in the preparation as well as other additives performing specific desired functions, i.e., coating agents, hardeners, plasticizers, viscosity-increasing agents, stabilizers, preservatives, dissolution speed-increasing compounds and other manufacturing addenda.

The concentration of the binding agent in this invention may range from about 0.0001 percent and up to about 95 percent of the weight of the composition with about 0.5 percent to about 35 percent being the most suitable range, depending on the type of compound used, viscosity desired, chemical catalyst added, compatibility of the materials employed, etc.

The preferred materials for use as bacteriostatic agents in the context of the present invention are any agent that prevents the development, destroys or interferes in a direct way with the life processes of bacteria, viruses or fungi. Examples of the suitable agents are:

1. Phenols, Gresols, Resolcinols and related compounds.

Phenol; substituded phenols—cresols, meta-cresylacetate, creosote, quaiacol, resorcinol, hexylresorcinol, pyrogallol, thymol, thymol iodide, picric acid, chlorinated phenols—dichlorophene, hexachlorophene, tars.

2. Alcohols and glycerols.
3. Aldehydes.

Formaldehyde, methenamine.

4. Acids.

Inorganic acids, chromic acids, benzoic acids, acetic acid, boric acid, salicylic acid, mandelic acid, fungicidal fatty acids.

5. Halogens and Halogen-containing compounds.

Iodine, iodoform, chlorine, sodium hypochloride, chlorinated lime, chloramines.

6. Oxidizing agents.

Peroxides, sodium perporate, potassium permanganate, zinc permanganate, potassium chlorate.

7. Heavy metals and their salts.

Mercury, mercuric chloride, miscellaneous ionizable mercuric salts, organic mercurials, silver, silver nitrate, silver lactate, silver picrate, silver proteins, silver halides, zinc oxide, zinc stearate, copper, copper sulfate.

8. Miscellaneous Commercial Products.

Commercial products available in the market such as TCC, DP-300, number several hundred either alone or in combination with some of the above mentioned compounds.

9. Surface-active compounds.

Benzalkonium chloride, benzethonium chloride, cetyl pyridinium chloride, sodium tetradecyl sulfate, sichlorobenzalkonium chloride, methylbenzethonium chloride, cetyl dimethyl ethyl ammonium bromide.

10. Dyes.

Azo dyes, acridene dyes, fluorescein dyes, phenolphthalein dyes, triphenylmethane dyes, miscellaneous dyes.

11. Miscellaneous Germicides and Fungicides.

Furan derivatives, nitrofurantoin, sulfur, sulfur dioxide, ichthamol, chrysarobin, anthralin, betanaphthol, balsams, volatile oils, chlorophyl.

12. Insecticides and Arachnicides.

DDT, benzene hexachloride, benzyl benzoate, miscellaneous arachnicides.

The toilet article 10 embodiment of the present invention dispersed, mixed or suspended in the hydrophilic binding agent may contain in addition flavoring agents, soap or synthetic detergents, thickeners, emulsifiers, dispersants, hardeners, plasticizers, water and/or organic solvents, and other mechanical aids. Some examples of flavoring agents useful in my invention are essential oils such as anise oil, cinnamon oil, clove oil, eucalyptol, eucalyptus oil, eugenol, menthol, methyl salicylate, peppermint oil and spearmint oil to name only a few; soap or synthetic detergents such as dioctyl sodium sulfosuccinate, sodiul alkyl sulfoacetate, sodium lauryl sulfate, sulfocolaurate and sodium lauroyl sarcosinate; thickening agents such as acacia, bentonite, carrageenan-Irish moss extractive, methyl cellulose, sodium carboxymethylcellulose, sterculia gum, tragacanth, guar gum, alginates, xanthene gums and other suitable naturally occurring or organic agents; emulsifiers of either anionic, cationic or nonionic type such as an ester, amide or sulfonamide (anionic), primary, secondary or tertiary amine salts with aliphatic or aromatic groups or nitrogen compounds such as quaternary ammonium compounds, quanidine and thiuronium salts (cationic) and polyethylene glycol, polyvinyl alcohol, polyethers, polyesters and polyhalides (nonionic); dispersants such as some of the emulsifiers and thickening agents listed above; hardeners in the form of fillers such as glass, carbon, cellulosic fillers, other carbohydrates (starch), calcium carbonate, metallic oxides, metallic powders, polymers, silica products, silicates and other inorganic compounds; plasticizers such as glycerin, propylene glycol, polyethylene glycol 4000, polyethylene glycol 1500, diethylene glycol monoethyl ether, sorbitol, polysorbate, polyoxyethylene sorbitan monolaurate, etc.; water and organic solvents such as halogen substituted amines, benzene derivatives, acetone compounds, alcohols, ketones, glycols, etc.

Additional helpful aids that can be employed in the formulation of the toilet article 10 are antioxidants such as alkylated phenols and bisphenols, alkylidene bis, tris and polyphenols, thio phenols, phenol condensation products, organic phosphites and phosphates, and miscellaneous products; antistatic agents, flame retardants, heat stabilizers, lubricants, organic peroxides, preservatives, silane adhesion promoters, and ultraviolet stabilizers.

It is important to note that in the concept of this invention it is not necessary to employ one or more of each additive in the formulation of the toilet article 10. The concentration and the type of agents used are dependent upon the consistency of the item, the solubility of the binding agent, the amount of the bacteriostatic agent necessary for the purpose intended and the coloring effect in the solution and may range from 0.0001% to 75% of the weight of the composition.

The term "bacteriostatic agent" in this invention is synonymous to and may be interchangeable with bacteriocide, germicide, fungicide, disinfectant and other terms commonly used to indicate growth control, either by killing or suppressing, of various bacteria and germs.

The invention will be further illustrated but is not intended to be limited by the following examples.

EXAMPLE 1

A bacteriostatic element is made up as follows: 6 Gr. of POLYOX WSR-N 750[1] is dissolved in acetone-water solvent containing 60 percent acetone and treated with 10 cc phenol. 3.00 cc of essential oil Cassis, 0.5 Gm of coloring agent FD&C Blue #1 and 2 Gm of thickener Guar gum was added to the solution. The element was cast on a glass mold containing 40 cc of the solution and dried for 10 minutes at 150° C. The formed element was placed in the toilet reservoir (tank) and the water flushed every ½ hour until coloring of the water disappears.
[1]Polyethylene oxide resin Union Carbide Corporation

EXAMPLE 2

A bacteriostatic element is made up as follows:
20 Gms. of GELVATOL 20-60[2] is dissolved in 100 cc water. To this solution 40 cc of acetone and 15 cc of phenol was added with gentle stirring. 15 Gms. of corn starch; 3 cc of Essential oil "peppermint"; 1 Gm of Duponal (sodium lauryl sulfate); and 1 Gm of coloring FD&C Blue #1 was now added. The element was cast and dried in the same way as in Example 1.
[2]Polyvinyl Alcohol resin Monsanto Company

EXAMPLE 3

A bacteriostatic element is made up as follows:
In 100 cc water is dissolved
20 Gms CARBOSET 525[3]
Z Gms sodium carbonate
10 cc phenol
1 Gm CMC (carboxylated methylcellulose)
3 cc essential oil "spearmint"
1 Gm FD&C Blue #1
Treated same as in Example 1.
[3]Acrylic resin B. F. Goodrich Chemical Co.

EXAMPLE 4

A bacteriostatic element is made up as follows:
75 cc of PHOPLEX TR-520[4]
20 cc phenol
20 cc water
40 cc ACRYSOL[4] (50% solution)
30 cc Ammonium hydrohyde, conc.
1 Gm FD&C Blue #1
3 cc essential oil "cassia".
Treated same as in Example 1.
[4]Acrylic resin Rohm and Haas Company

EXAMPLE 5

A bacteriostatic element was made up as follows:
Same as Example 1 but FD&C Blue #1 is substituted by 1% solution of Quinoline blue (cyanine) indicator at pH lower than 6.0.

EXAMPLE 6

A bacteriostatic element is made up as follows:
Same as Example 2 but FD&C Blue #1 is substituted by 1% solution of bromothymol blue indicator. at pH lower than 6.0.

EXAMPLE 7

A bacteriostatic element formulated as follows:
Same as in Example 1 but FD&C Blue #1 is substituted by 1% solution of bromcresol green at pH lower than 3.5.

EXAMPLE 8

A bacteriostatic element formulated as follows:
Same as in Example 3 but FC&C Blue #1 is substituted by 1% solution of bromcresol purple at pH lower than 5.0.

EXAMPLE 9

A bacteriostatic element formulated as follows:
To 100 cc water was added
2 Gms POLYOX WSR-N-750

5 cc glacial acetic acid
50 cc acetone
20 cc phenol
4 Gms gelatin 40 cc of this solution was poured into a glass mold and dried at room temperature for 48 hours.

EXAMPLE 10

A bacteriostatic element was prepared the same as in Example 9 but 20 cc of o-phenol phenol was substituted for the 20 cc of phenol.

EXAMPLE 11

A bacteriostatic element was formulated as in Example 9 but 20 cc of dichlorophene was substituted for 20 cc of phenol.

EXAMPLE 12

A bacteriostatic element formulated as follows:
To 100 cc of water was added
30 Gms of GELVATOL 20-30
50 cc methyl alcohol
20 cc phenol
3 Gms KELGIN XL[5]
15 Gms corn starch
3 cc menthol
1 Gm FD&C Red #3
[5]Sodium alginate Kelco Company 40 cc of this solution was cast into a glass mold and allowed to dry at room temperature for 48 hours.

EXAMPLE 13

A bacteriostatic element was formulated as follows:
To 100 cc of water was added
6 Gms POLYOX WSR-250
6 Gms GELVATOL 20-60
3 Gms Acacia (gum Arabic)
1 Gm iodine
4 cc Essential Oil
3 Gm FD&C Green #3

Resin and iodine are ground together in a pebble mill for 26 hours and then cast on a glass mold and dried for 24 hours at room temperature.

EXAMPLE 14

A bacteriostatic element was made up as follows:
To 100 cc of water was added
3 Gms KELGIN XL
2 Gms Guar gum
1 Gm calcium carbonate
2 Gms bromine
1 Gm FD&C Blue #2

50 cc of the solution was extruded at temperatures between 100°-400° F. and the elements cooled by the conventional cooling trains.

This invention makes use of certain compounds which when in solution render the solution a certain color. The colorant, or color additive, in the context of the present invention is any dye, pigment, or other substance made by a process of synthesis or similar artifice, or extracted, isolated or otherwise derived, with or without intermediate or final change of identity, from a vegetable, animal, mineral or other source and that, when added or applied to a resin or any other substance or compound useful in this invention, is capable, alone or through reaction with another substance, of imparting a color thereto. This definition shall apply to substances capable of imparting a color to a container for food, drug and cosmetic when customary or foreseeable handling or use of the container may reasonably be expected to result in the transmittal of the color to the contents of the package or any part of the surrounding or proximal media.

This definition includes any substance or mixture of substances having a Color Index of from 1 and up to 100,000 and may be either in acid, basic, direct, food, ingrain, mordant, natural, pigment or solvent composition or form.

There are approximately 1,000 different coloring agents available in the commercial market today either as food colorants, drug additives a cosmetic colorants, therefore, it is beyond the scope of this invention to list each individual coloring agent separately. For that reason only the main groupings of dyes and pigments, and some examples, are listed in this disclosure but it should be understood that some unnamed colorants which are excluded from the list remain within the scope and intent of this invention.

The useful colorants in this invention are the azo dyes; pyridium, acrydine; flurescein (pyronine); phenolphthalein; triphenylmethane (rosaniline); metholine blue; furan derivatives; nitrofurantoin and miscellaneous dyes. Some useful FD&C and D&C colors are FD&C Blue #1 and #2; FD&C Green #3 and Fast Green FCF; FD&C Yellow #5 and #6; FD&C Red #2, #3 and #40; and FD&C Lakes; D&C Blue #4, #6 and #9; D&C Green #5, #6 and #8; D&C Orange #4, #5, #10, #11 and #17; D&C Red #6, #7, #8, #9, #10, #11, #12 and #13 and mixtures thereof.

The concentration and type of compound being used depends upon the color desired and the intensity of color produced and may be in the range of about 0.05% and up to about 50% with 0.25% and 10% being the preferred range.

To adjust the pH of the formulations of this invention basic and acid compounds are employed. Some examples of these compounds are aluminum hydroxide, sodium hydroxide, magnesium hydroxide, potassium hydroxide, borox, sodium bicarbonate, potassium bicarbonate, sodium carbonate, potassium carbonate, the tribasic and dibasic phosphates of calcium, magnesium and sodium, aluminum phosphate, basic aluminum carbonate, acetic acid, hydrochloric acid, nitric acid and any other substance that in aqueous solution gives either acid or basic reaction to litmus.

EXAMPLE 15

A bacteriostatic element was made up as follows:
To 100 cc of Water as added
6 Gms SCS-MV[6]
15 cc O-phenol-phenol
2 Gms potassium chloride
10 Gms starch
0.5 Gms FD&C Blue #2
4 cc methyl salycilate
Sodium Cellulose Sulfate Kelco Company A series of tests were conducted using different combinations of the preferred hydrophylic binding agents. The comparative results of the various hydrophylic materials used, including the Example 1-15, are shown in Table 1 below.

TABLE 1

| HYDROPHYLIC MATERIAL | BACTERIOSTAT | COLORANT | OTHER* | DURATION** |
|---|---|---|---|---|
| 1. Poly(ethylene Oxide) POLYOX WSR-N-750 | Phenol | FD&C Blue #1 | Guar gum | 32 |
| 2. Polyvinyl alcohol GELVATOL 20-60 | Phenol | FD&C Blue #1 | Corn Starch | 34 |
| 3. Polyacrylic acid CARBOSET 525 | Phenol | FD&C Blue #1 | CMC | 21 |
| 4. Polyacrylic acid RHOPLEX TR-520 | Phenol | FD&C Blue | Acrysol | 19 |
| 5. Poly(ethylene oxide) | Phenol | Quinoline blue | Guar gim | 32 |
| 6. Polyvinyl alcohol | Phenol | Bromothymol blue | Corn Starch | 34 |
| 7. Poly(ethylene oxide) | Phenol | Bromcresol green | Guar gum | 32 |
| 8. Polyacrylic acid | Phenol | Bromcresol purple | CMC | 21 |
| 9. Poly(ethylene oxide) | Phenol | FD&C Blue #1 | Gelatin | 20 |
| 10. Poly(ethylene oxide) | o-phenol phenol | FD&C Blue #1 | Gelatin | 20 |
| 11. Poly(ethylene oxide) | Dichlophene | FD&C Blue #1 | Gelatin | 20 |
| 12. Polyvinyl alcohol | Phenol | FD&C Red #3 | Alginate + starch | 46 |
| 13. Poly(ethylene oxide)+ | Iodine | FD&C Green #3 | Gum arabic | 36 |
| 14. Polyvinyl alcohol | | | | |
| 15. Sodium Alginate | Bromine | FD&C Blue #2 | Guar gum + calcium carbonate | 36 |
| 16. Sodium Cellulose Sulfate | o-phenol phenol | FD&C Blue #2 | Starch + KCl | 35 |
| 17. Polyvinyl alcohol | Cresol | FD&C Blue #1 | Borax | 35 |
| 18. Polyvinyl alcohol | Phenol | FD&C Blue #1 | Borax + talc | 36 |
| 19. Poly(ethylene oxide) | Hexachlorophene | FD&C Blue #1 | Borax + guar gum | 38 |
| 20. Polyurethane | Phenol | FD&C Blue #1 | Guar gum | 28 |
| 21. Polyurethane | Phenol | FD&C Blue #1 | Borax + guar gum | 35 |
| 22. Polyacrylamide | Phenol | FD&C Blue #1 | Alginate | 28 |
| 23. Polyacrylamide | Phenol | FD&C Blue #1 | Borax + alginate | 32 |
| 24. Poly(vinyl pyrrolidone) | Phenol | FD&C Blue #1 | Guar gum | 26 |
| 25. Poly(vinyl pyrrolidone | Phenol | FD&C Blue #1 | Borax + guar gum | 32 |
| 26. Copolymer acrylic acid and ethyl acrylic | Cresol | Malachite Gr. | CMC | 18 |
| 27. Propylene Glycol alginate | Cresol | FD&C Red #40 | Chrome ions | 20 |
| 28. Propylene Glycol alginate | Cresol | FD&C Red #40 | None | 8 |
| 29. POLYOX + GELVATOL | Hexachlorophene | FD&C Blue #1 | None | 18 |
| 30. POLYOX + GELVATOL | Hexachlorophene | FD&C Blue #1 | Borax | 32 |
| 31. POLYOX + CARBOSET | Hexachlorophene | FD&C Blue #1 | None | Insoluble |
| 32. GELVATOL + CARBOSET | Phenol | FD&C Blue #1 | None | 28 |

*Additive which has effect on the solubility, hardness or viscosity of the element.
**The time in days that was necessary to dissolve the entire element.

All samples used in the test were cast on a glass mold containing 40 cc of the solution and dried for at least 10 minutes at 150° C.

Tests were also conducted employing the same combinations and concentrations as listed in TABLE 1 but cure of the samples was affected at room temperature at ambient humidity. In each occasion these samples were inferior to the heat dried elements in solubility, consistency and duration of cure. Many samples, particularly ones not containing chemical additives, had to be dried for 7 to 10 days without functional improvement.

The results in TABLE 1 indicate that all samples were effective from 8 up to 38 days and that increasing the amount of additive and total solids in the solution improves the formulations, drying and prolongs solubility in water. The most functional combinations are ones containing poly(ethylene oxide), polyvinyl alcohol, sodium celullose sulfate, polyurethane, polyacrylamide, poly(vinyl pyrrolidone) and sodium alginate either as the main components or as a part in the formulation of the element.

The element of this invention may contain additional aids such as dispersants, antioxidants, plasticizers, stabilizers, hardeners, soaps and/or detergents, fillers, organic solvents and other processing and supportive agents. Examples of each group of additives was listed above and the concentration of each may vary from about 0.0001 percent and up to 80 percent (such as in the case of fillers) of the total weight of the element.

The novel element of the present invention covers numerous different designs, shapes, sizes and formulations. It may be square in shape or circular or any other configuration in between; it may range in weight from about 1 Gram and up to but not limited to 500 Grams; it may be solid, semi-solid; semi-fluid or fluid in consistency; it may be colored using any dye or pigment or it may be in its natural state of hue.

The invention has been described in detail with particular reference to a preferred embodiment thereof but it will be understood that variations and modifications can be effected within the spirit and scope of the invention as described thereinabove and as defined in the appended claims.

I claim:

1. A method of disinfecting the water in a toilet, said toilet having a water tank, a bowl, and a drain connecting said tank to said bowl, water passing through said drain during flushing only, said drain having an upright drain tube through which water passes during flushing only, said method comprising the steps of:

disposing in said drain a formed, water soluble toilet element comprising a binding agent and an effectie amount of bacteriostatic agent;

positioning in said drain a mesh drain basket, said mesh basket being adapted to allow water with dissolved toilet element to pass into said bowl but to otherwise prevent said formed toilet element from passing into said bowl, whereby the water passing into said bowl is treated but said water soluble element is conserved by dispersing only during flushing; and introducing said bacteriostatic agent into said bowl during flushing only.

2. A method of disinfecting the water in a toilet, said toilet having a water supply, a bowl, and a drain connecting said water supply to said bowl, water passing through said drain during flushing only, comprising the steps of:

disposing in said drain a toilet element comprising binding agent and an effective amount of bacteriostatic agent; and introducing said bacteriostatic agent into said bowl during flushing only.

3. A method of disinfecting the water in a toilet as defined in claim 2 and further comprising the step of positioning in said drain a mesh drain basket, said mesh basket being adapted to allow water with dissolved toilet element to pass into said bowl but to otherwise prevent said toilet element from passing into said bowl.

4. A method of disinfecting the water in a toilet as defined in claim 2 wherein said drain has an upright drain tube through which water passes during flushing only and wherein the step of disposing a toilet element in said drain comprises disposing said toilet element in said upright drain tube.

* * * * *

UNITED STATES PATENT AND TRADEMARK OFFICE
CERTIFICATE OF CORRECTION

PATENT NO. : 4,229,410
DATED : October 21, 1980
INVENTOR(S) : Carl M. Kosti

It is certified that error appears in the above–identified patent and that said Letters Patent are hereby corrected as shown below:

Column 9, No. 4, under the column "Colorant" after "Blue", insert --#1--.

Signed and Sealed this

Twenty-seventh Day of January 1981

[SEAL]

Attest:

RENE D. TEGTMEYER

Attesting Officer     Acting Commissioner of Patents and Trademarks